US012734245B2

(12) United States Patent
Rivera Gil et al.

(10) Patent No.: US 12,734,245 B2
(45) Date of Patent: Sep. 15, 2026

(54) TREATMENT AND/OR DIAGNOSIS OF A CANCER TYPE CHARACTERIZED BY EXPRESSING ZINC TRANSPORTER ZIP4

(71) Applicant: Universitat Pompeu Fabra, Barcelona (ES)

(72) Inventors: Pilar Rivera Gil, Barcelona (ES); Rubén Vicente García, Barcelona (ES); Ruixue Xu, Barcelona (ES)

(73) Assignee: Universitat Pompeu Fabra, Barcelona (ES)

( * ) Notice: Subject to any disclaimer, the term of this patent is extended or adjusted under 35 U.S.C. 154(b) by 850 days.

(21) Appl. No.: 17/909,885

(22) PCT Filed: Mar. 10, 2021

(86) PCT No.: PCT/EP2021/056036
§ 371 (c)(1),
(2) Date: Sep. 7, 2022

(87) PCT Pub. No.: WO2021/180780
PCT Pub. Date: Sep. 16, 2021

(65) Prior Publication Data
US 2023/0211005 A1 Jul. 6, 2023

(30) Foreign Application Priority Data
Mar. 10, 2020 (EP) .................................... 20382172

(51) Int. Cl.
*A61K 47/68* (2017.01)
*A61K 41/00* (2020.01)
*A61K 47/69* (2017.01)

(52) U.S. Cl.
CPC ...... *A61K 47/6843* (2017.08); *A61K 41/0052* (2013.01); *A61K 47/6925* (2017.08); *A61K 47/6929* (2017.08)

(58) Field of Classification Search
CPC ............ A61K 47/6843; A61K 41/0052; A61K 47/6925; A61K 47/6929; A61K 47/6859; A61K 47/6923
See application file for complete search history.

(56) References Cited

FOREIGN PATENT DOCUMENTS

WO WO 2009/062104 A2 5/2009

OTHER PUBLICATIONS

Groff, Katherine et al., "Modern affinity reagents: Recombinant antibodies and aptamers" Biotechnology Advances, 2015, pp. 1787-1798, vol. 33.
Hashimoto, Ayako et al., "Properties of Zip4 accumulation during zinc deficiency and its usefulness to evaluate zinc status: a study of the effects of zinc deficiency during lactation" American Journal of Physiology—Regulatory Integrative and Comparative Physiology, Mar. 2016, pp. R459-R468, vol. 310, No. 5.
(Continued)

*Primary Examiner* — Stacey N Macfarlane
(74) *Attorney, Agent, or Firm* — KNOBBE, MARTENS, OLSON & BEAR, LLP

(57) ABSTRACT

Treatment and/or diagnosis of a cancer type characterized by expressing zinc transporter ZIP4. The present invention is directed to nanocarriers functionalized with a ligand capable to bind to the extracellular domain of zinc transporter ZIP4, for use in the treatment and/or diagnosis of a cancer type characterized by expressing ZIP4.

12 Claims, 9 Drawing Sheets

Specification includes a Sequence Listing.

A

B

(56) References Cited

OTHER PUBLICATIONS

Marx, Vivien et al., "Calling the next generation of affinity reagents" Nature Methods, Sep. 2013, pp. 829-833, vol. 10, No. 9.
Ong, Shao-En et al., "Identifying the proteins to which small-molecule probes and drugs bind in cells" PNAS, Mar. 2009, pp. 4617-4622, vol. 106, No. 12.
Yu, Xianjun et al., "Targeted drug delivery in pancreatic cancer" Biochimica et Biophysica Acta, 2010, pp. 97-104, vol. 1805.
International Search Report for PCT/EP2021/056036 dated Jun. 8, 2021.

A

B

C

D

E

A

B

C

D

A

B mAb clone 62

C

D

TREATMENT AND/OR DIAGNOSIS OF A CANCER TYPE CHARACTERIZED BY EXPRESSING ZINC TRANSPORTER ZIP4

CROSS REFERENCE TO RELATED APPLICATIONS

This application is a U.S. National Phase Application of PCT International Application Number PCT/EP2021/056036, filed on Mar. 10, 2021, designating the United States of America and published in the English language, which is an International Application of and claims the benefit of priority to European Patent Application No. 20382172.3, filed on Mar. 10, 2020. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52 (e). The name of the ASCII text file for the Sequence Listing is SeqList-HOFM023-001APC.txt, the date of creation of the ASCII text file is Sep. 1, 2022, and the size of the ASCII text file is 12 KB, updated by a file named SeqList-HOFM023-001APC_Corrected.txt, created on Feb. 1, 2023, which is 11,478 bytes in size.

FIELD OF THE INVENTION

The present invention pertains to the medical field. Particularly, the present invention is directed to nanocarriers functionalized with a ligand capable to bind to the extracellular domain of zinc transporter ZIP4, for use in the treatment and/or diagnosis of a cancer type characterized by expressing ZIP4.

STATE OF THE ART

Pancreatic cancer is the $4^{th}$ leading cause of cancer-related deaths. The relative survival after 5 years is 8% considering the period between 2007-2013. By 2030, researchers project that pancreatic cancer will become the $2^{nd}$ leading cause of cancer related death in the US after lung cancer, surpassing colorectal, breast and prostate cancer. The reason for these dismal results is a failed diagnosis and an inefficient therapeutic strategy.

The lack of identification of a high-risk population, effective screening methods for early diagnosis and an inefficient treatment strategy is responsible for these dismal results. Most patients are diagnosed with an advanced/metastatic stage of the disease, for whom chemotherapy is inefficient. Currently there are no effective strategies for detecting pre-neoplastic/early invasive lesions. Advanced tumors are diagnosed and staged through imaging techniques such as ultrasound, computed tomography (CT) and magnetic resonance imaging. Crosssectional abdominal CT imaging with radiocontrast agents (iodine or barium sulfate derivatives) is the preferred initial modality in patients with clinical suspicions. However, CT lacks accuracy and specificity. This is crucial to avoid false positive results (tumor identification). Recently, gold nanoparticles have shown higher contrast at lower X-ray dose and higher resolution (molecular imaging) because of higher absorbance than standard agents.

Targeted drug delivery for the treatment of cancers is one of the most anticipated and discussed benefits of nanotechnology-enabled medicine as it offers a level of accuracy in delivering drugs that far surpasses present methods. Typically, over 90% of a drug is wasted in the body, which leads to unwanted side effects. Modern chemotherapy bombards patients with drugs in the hope that tumorous cells will be destroyed. The lack of specificity of current drug delivery techniques mean patients' healthy cells are destroyed indiscriminately along with cancer cells.

Pancreatic cancer management implies surgical resection as the only definitive treatment strategy. Unfortunately, only 10-20% of patients will have resectable tumors. Adjuvant chemotherapy with gemcitabine, or a combination with paclitaxel is given after surgery because it increases the survival rate. Induction chemotherapy with gemcitabine plus Nab-paclitaxel or FOLFIRINOX (5-flurouracil, leucovorin, irinotecan, oxaliplatin) is given to fit patients with metastasis or unresectable tumours, however, with low impact on survival rates. Neoadjuvant chemotherapy where chemotherapy and radiotherapy are given prior to surgery is currently the option for borderline resectable tumors. Pancreatic tumor poor prognosis is because of late detection (inefficient imaging and blood markers detection) and a high resistance to chemotherapy, which has been associated to its hostile tumor microenvironment. Improving pancreatic cancer patients' outcome is an important unmet clinical need.

Consequently, there is an unmet medical need of finding new strategies for the early detection and treatment of pancreatic cancer.

The present invention is directed to solve these problems by providing targeting nanocarriers to pancreatic tumor cells to enable local delivery of the therapeutic and to improve early diagnosis of tumor lesions.

DESCRIPTION OF THE INVENTION

Brief Description of the Invention

Zinc transporter ZIP4 is a transmembrane protein which in humans is encoded by the SLC39A4 gene. ZIP4 is overexpressed in human pancreatic cancer and contributes to tumor progression by accumulation of intracellular zinc and stimulation of cell proliferation, endothelial mesenchymal transition and cancer progression. Thus, overexpression of ZIP4 is considered a malignant factor for pancreatic cancer progression.

The present invention in focused on providing a new approach for the early detection and treatment of a cancer type characterized by expressing ZIP4, preferably pancreatic cancer.

Particularly, the inventors of the present invention have developed specific nanocarriers which are functionalized with a ligand capable to bind to the extracellular domain of zinc transporter ZIP4. Since the nanocarrier comprises an active ingredient, preferably an anti-cancer drug, which is effective in the treatment of said cancer types, these nanocarriers can be used in the treatment of a cancer type characterized by expressing ZIP4, for example pancreatic cancer. On the other hand, the nanocarrier comprises a contrast agent (gold) for molecularly targeted computed tomography (CT) diagnosis of a cancer type characterized by expressing ZIP4, for example pancreatic cancer.

So, the first embodiment of the present invention refers to a nanocarrier functionalized with a ligand capable to bind to the extracellular domain of Zinc transporter ZIP4, for use in the treatment and/or diagnosis of a cancer type characterized by expressing ZIP4.

In a preferred embodiment, the ligand is an antibody obtained by an in vitro method which comprises: a) administering the immunogen of SEQ ID NO: 1, which pertains to the entire extracellular domain of Zinc transporter ZIP4, to an animal model to induce the generation of antibodies, and b) obtaining the antibodies thus generated. So, in a preferred embodiment, the antibody obtained (after the administration of the immunogen of SEQ ID NO: 1 to the animal model) is used as a ligand of the nanocarrier.

In a preferred embodiment, the cancer to be treated is a ZIP-related tumor, preferably pancreatic cancer. Nevertheless, since ZIP4 is reported to be differentially expressed in multiple cancers, the present invention can be extrapolated to the treatment of any type of cancer characterized by expressing Zinc transporter ZIP4, for example: Ovarian, lung, breast and hepatic tumors.

In a preferred embodiment, the nanocarrier consists of hollow nanocapsules comprising a biodegradable material on a layer basis around a sacrificial template with a size lower than 500 nm. In a preferred embodiment, the ligand comprises a moiety with molecular recognition properties. In a preferred embodiment, the ligand is selected from the list comprising: antibodies, minibodies, nanobodies, Fab fragments and aptamers. In a preferred embodiment, the ligand is a monoclonal or a polyclonal antibody. In a preferred embodiment, the nanoparticle is a plasmonic nanoparticle. In a preferred embodiment, the nanoparticle is a photothermal probe. In a preferred embodiment, the nanocarrier comprises an active ingredient, preferably an anticancer drug. In a preferred embodiment, the nanocarrier comprises a contrast agent for X-ray-associated diagnostic techniques. In a preferred embodiment, the nanocarrier is characterized by comprising nanostructured gold as contrast agent for X-ray-associated diagnostic techniques. In a preferred embodiment, the nanocarrier is able to transport, accumulate and deliver an active ingredient to any cancer type expressing ZIP4.

As explained above, the nanocarrier can be functionalized with gold and they can act as a theragnostic agent suitable for producing pathological heat levels and for acting as contrast agents for computed tomography. In addition, such nanocarriers shall be functionalized so that they only identify certain tumor cells thus allowing specific targeting. Such nanocarriers shall be functionalized with a molecule capable of interacting or binding the ZIP4 transporter intracellular or extracellular domain.

The second embodiment of the present invention refers to the above mentioned nanocarrier for use in a method for in vivo diagnosis of pancreatic cancer.

The third embodiment of the present invention refers to a pharmaceutical composition comprising the above mentioned nanocarrier, and optionally pharmaceutically acceptable excipients, for use in the treatment of a cancer type expressing ZIP4, preferably pancreatic cancer. Alternatively, this embodiment refers to a method for treating a cancer type expressing ZIP4, preferably pancreatic cancer, which comprises the administration of a therapeutically effective amount of the pharmaceutical composition.

The fourth embodiment of the present invention refers to a nanocarrier functionalized with an affinity reagent specifically binding the extracellular domain of Zinc transporter ZIP4 consisting of the sequence defined by SEQ ID NO: 1, for use in the treatment and/or diagnosis of a cancer type characterized by expressing ZIP4.

In a preferred embodiment the nanocarrier for use, according to the present invention, is functionalized with an affinity reagent which is an antibody obtained by an in vitro method which comprises: a) administering the immunogen of SEQ ID NO: 1, which pertains to the entire extracellular domain of Zinc transporter ZIP4, to an animal model in order to induce the generation of antibodies, and b) obtaining the antibodies thus generated.

In a preferred embodiment the nanocarrier for use, according to the resent invention, is functionalized with an affinity reagent which is a monoclonal antibody characterized in that it comprises a light chain variable region (VL) and a heavy chain variable region (VH), wherein said VH comprises HCDR1, HCDR2 and HCDR3 polypeptides and VL comprises LCDR1, LCDR2 and LCDR3 polypeptides and, wherein HCDR1 consists of the sequence SEQ ID NO: 4, HCDR2 consists of the sequence SEQ ID NO: 5, HCDR3 consists of the sequence SEQ ID NO: 6, LCDR1 consists of the sequence SEQ ID NO: 9, LCDR2 consists of the sequence KVS and LCDR3 consists of the sequence SEQ ID NO: 10.

In a preferred embodiment the nanocarrier for use, according to the resent invention, is functionalized with an affinity reagent which is a monoclonal antibody characterized in that it comprises a light chain variable region (VL) and a heavy chain variable region (VH), wherein said VH comprises HCDR1, HCDR2 and HCDR3 polypeptides and VL comprises LCDR1, LCDR2 and LCDR3 polypeptides and, wherein HCDR1 consists of the sequence SEQ ID NO: 13, HCDR2 consists of the sequence SEQ ID NO: 14, HCDR3 consists of the sequence SEQ ID NO: 15, LCDR1 consists of the sequence SEQ ID NO: 18, LCDR2 consists of the sequence STS and LCDR3 consists of the sequence SEQ ID NO: 19.

In a preferred embodiment, the nanocarrier of the invention is used to treat a ZIP-related tumor, preferably pancreatic cancer.

In a preferred embodiment, the nanocarrier of the invention consists of hollow nanocapsules comprising a biodegradable material on a layer basis around a sacrificial template with a size lower than 500 nm.

In a preferred embodiment, the nanocarrier of the invention is characterized in that it comprises an active ingredient, preferably an anti-cancer drug.

In a preferred embodiment, the nanocarrier of the invention is characterized in that it comprises a contrast agent for X-ray-associated diagnostic techniques.

In a preferred embodiment, the nanocarrier of the invention is able to transport and deliver an active ingredient to any cancer type expressing ZIP4.

In a preferred embodiment, the nanocarrier of the invention is used in a method for in vivo diagnosis of pancreatic cancer.

The fifth embodiment of the present invention refers to a monoclonal antibody, or fragment thereof, specifically binding the extracellular domain of Zinc transporter ZIP4 consisting of the sequence defined by SEQ ID NO: 1.

In a preferred embodiment, the monoclonal antibody, or fragment thereof, of the invention is characterized in that it comprises a light chain variable region (VL) and a heavy chain variable region (VH), wherein said VH comprises HCDR1, HCDR2 and HCDR3 polypeptides and VL comprises LCDR1, LCDR2 and LCDR3 polypeptides and, wherein said VH comprises HCDR1, HCDR2 and HCDR3 polypeptides and VL comprises LCDR1, LCDR2 and LCDR3 polypeptides and, wherein HCDR1 consists of the sequence SEQ ID NO: 4, HCDR2 consists of the sequence SEQ ID NO: 5, HCDR3 consists of the sequence SEQ ID NO: 6, LCDR1 consists of the sequence SEQ ID NO: 9, LCDR2 consists of the sequence KVS and LCDR3 consists of the sequence SEQ ID NO: 10.

In a preferred embodiment, the monoclonal antibody, or fragment thereof, of the invention is characterized in that it comprises a light chain variable region (VL) and a heavy chain variable region (VH), wherein said VH comprises HCDR1, HCDR2 and HCDR3 polypeptides and VL comprises LCDR1, LCDR2 and LCDR3 polypeptides and, wherein HCDR1 consists of the sequence SEQ ID NO: 13, HCDR2 consists of the sequence SEQ ID NO: 14, HCDR3 consists of the sequence SEQ ID NO: 15, LCDR1 consists of the sequence SEQ ID NO: 18, LCDR2 consists of the sequence STS and LCDR3 consists of the sequence SEQ ID NO: 19.

The sixth embodiment of the present invention refers to a nanocarrier functionalized with a monoclonal antibody as defined in any of the previous embodiments.

The seventh embodiment of the present invention refers to a pharmaceutical composition comprising the monoclonal antibody as defined in any of the previous embodiments or the nanocarrier functionalized with a monoclonal antibody as defined in any of the previous embodiments, and optionally pharmaceutically acceptable excipients. Alternatively, this embodiment refers to a method for treating a cancer type expressing ZIP4, preferably pancreatic cancer, which comprises the administration of a therapeutically effective amount of the pharmaceutical composition.

For the purpose of the present invention, the following terms are defined:

By "affinity reagent" it is understood any biological molecule (for instance antibodies, minibodies, nanobodies and aptamers; or any part thereof including Fab, CDR, scFv, etc.) that specifically binds to a target molecule [Katherine Groff et al., 2015. *Modern affinity reagents: Recombinant antibodies and aptamers. Biotechnology Advances*. Volume 33, Issue 8, December 2015, Pages 1787-1798] [Vivien Marx et al., 2013. *Calling the next generation of affinity reagents. Nature Methods* volume 10, pages 829-833 (2013)].

By "fragment" of the antibody of the invention is understood any fragment as understood by the person skilled in the art, particularly any fragment which can be used to bind a target molecule, more preferably any individual complementarity determining regions (CDR) or single chain antibody fragment (scFv).

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

"Pharmaceutically acceptable excipient or carrier" refers to an excipient that may optionally be included in the compositions of the invention and that causes no significant adverse toxicological effects to the patient.

By "therapeutically effective dose or amount" of a pharmaceutical composition comprising the above mentioned nanocarrier is intended an amount that, when administered as described herein, brings about a positive therapeutic response in a subject having cancer. The exact amount required will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein.

DETAILED DESCRIPTION OF THE INVENTION

Example 1. Material and Methods

Example 1.1. Nanocarrier Design

Figure 1:
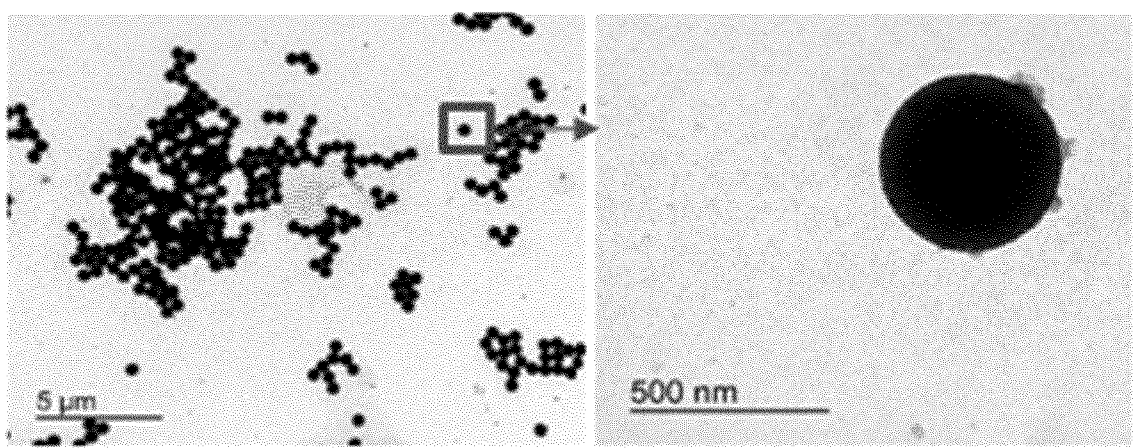
FIG. 1. Characterization of NC-antiZIP4 and PTX-BSA NP synthesis. A) Transmission electron microscopy of the nanocapsules (NC) placed on a metal grid. The scale bar represents 5 μm and 500 nm. B) Confocal image of NC-antiZIP4 incubated with Alexa Fluor 488 goat anti-rabbit IgG (antiIgG488). The scale bar represents 5 μm and 0.5 μm, respectively. C) Emission of the NC (blue line) (aprox. 590 nm) and of NC coupled to secondary IgG (488 nm). NC without the antibody (purple) or with PEG (green) showed no fluorescence for the antibody. D) Dynamic light scattering (DLS) measurements showing the hydrodynamic diameter of BSA NPs and Paclitaxel-loaded BSA (PTX NPs) both synthesized under pH 7.4. Picture shows BSA NPs (left) and PTX-BSA NPs. E) Zeta potential showing the different net surface charges of the BSA NPs and BSA-PTX NPs.
Figure 1:
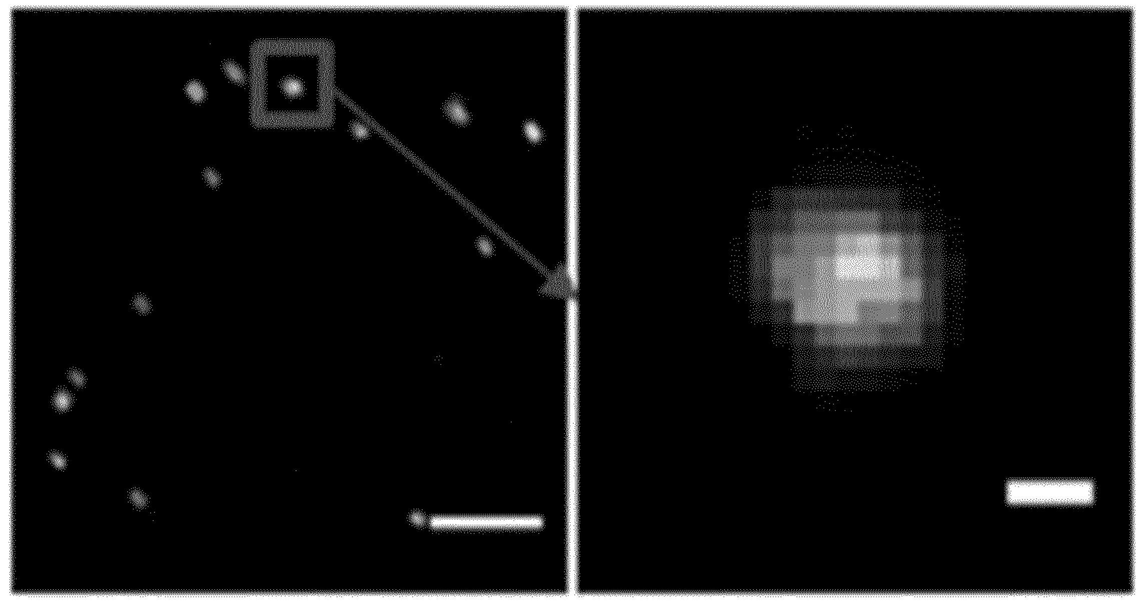
Figure 1:
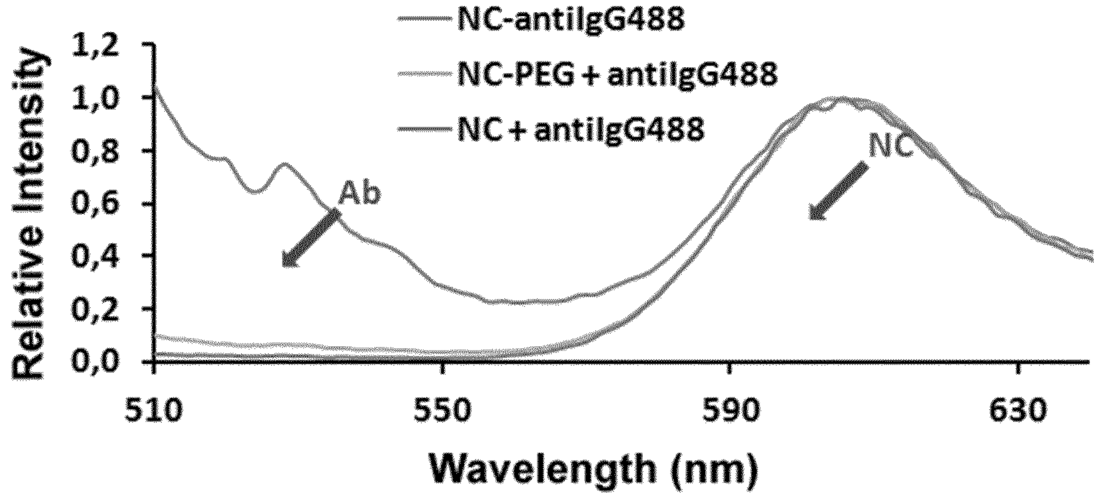
Figure 1:
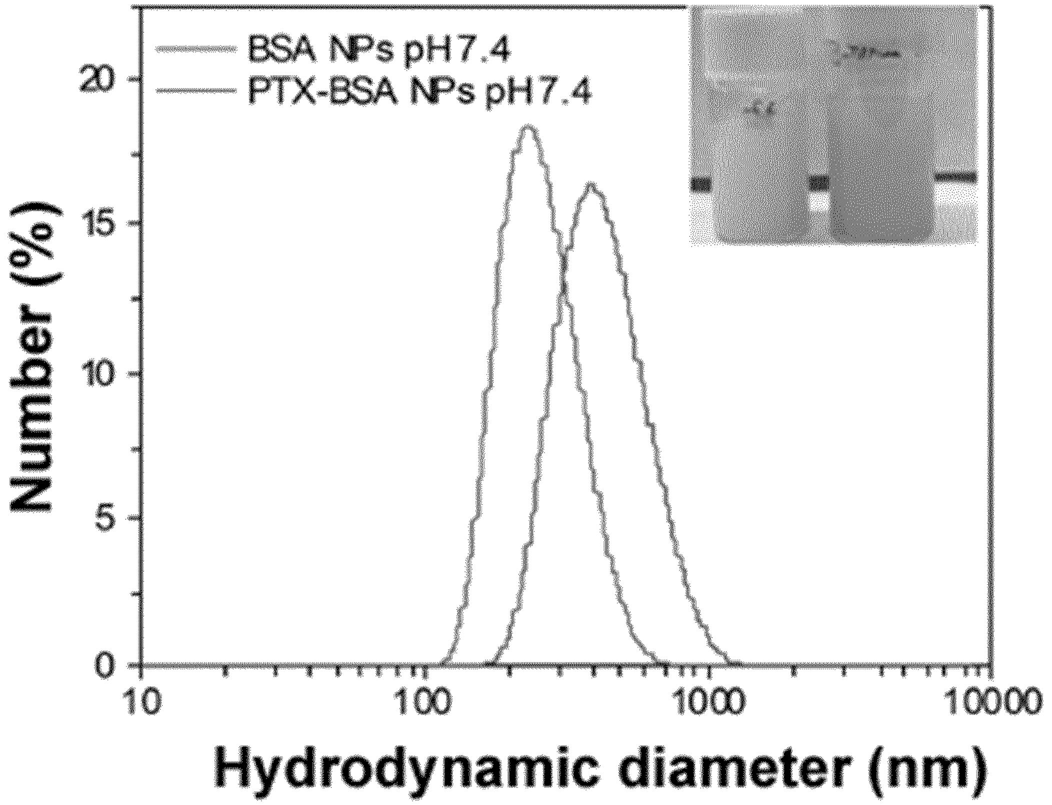
Figure 1:
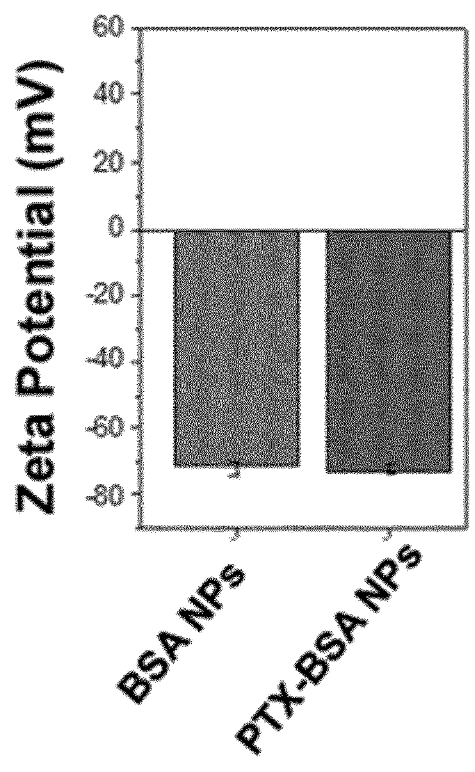

The nanocarrier is a biocompatible silica hollow nanocapsule. The nanocarrier synthesis mainly comprises 6 synthetic steps which are detailed below. Noteworthy that gold seed deposition and growth and the template type are steps that can be avoided depending on the application. For example, for the therapy, no gold is entrapped within the capsules and the polystyrene template is changed by the albumin nanoparticles conjugated to the paclitaxel acting as template:

1—Scaffold Synthesis:

250 ml of $H_2O$ bubbled with Ar for 4 h
0.75 g PVP K30 (Mw 55000)
0.64 g AIBA (iniziator)
Wait until the solution reach 70° C.
Reflux and Ar flux, stirring 300 rpm
25 g Styrene
24 h of reaction Washing Cycles (7500 Rpm, 30 Min)

2—Gold Seeds Deposition Due to Electrostatic Interactions Via Layer by Layer Protocols onto the Scaffold Surface:

I. Previous Polystyrene Functionalization via layer by layer technique: providing the necessary surface charge to the scaffold for later gold seed deposition:

5 ml of PS solution (6%) (0.33 g of PS) added drop by drop to 5 ml of ethanol in the ultrasound bath (no more than 40° C.), wait 5 min.

The previous solution (polystyrene in a mixture ethanol water) was added drop by drop to 50 ml of PSS solution (1 mg/ml in 0.5 M of NaCL) under sonication, keep it for 10 min in the ultrasound bath, and after that, 30 min of incubation time.

This solution was washed (3 centrifugation cycles) at 4000 rpm for 30 min.

The same protocol was repeated for PDDA, PSS, and PDDA again.

II. Gold seeds Synthesis:

45.5 ml of Milli Q water, followed by subsequent addition of reagents in the described order: NaOH solution (0.2M, 1.5 ml), THPC solution 1 ml, wait for 2 min (basic hydrolysis of THPC), and then the Chloroauric acid solution was added quickly in one-pot, the solution color turn to deep brown immediately, continue stirring around 10 mins.

III. Gold seed deposition onto Polystyrene surface was carried out by mixing Polystyrene-PSS-PDDA-PSS-PDDA nanoparticles (0.85 mg/ml), sonicate for a 5 min, followed by the addition of Au-seed nanoparticles dropwise under sonication in about 5 mins, incubation time 1 h for the completely gold nanoparticles deposition due to electrostatic interactions.

3—Silica Coating Via Stober Protocol Modification:

I. 400 μl of 110 mg/ml PVP is added to PS@Au-seeds suspension (0.85 mg/ml, 5 ml), after 2-3 h with stirring, the excess of PVP was removed by centrifugation. Ultracentrifuge with 6000 rpm, 15 mins, after the first centrifugation cycle the supernatant was removed and the sample was redispersed in MillQ water, in the following 2 centrifugations cycles the sample was redisperse and washed with ethanol.

II. When the excess PVP was removed, the pellet obtained was redispersed in 10 ml of 4.2% (v/v) ethanol solution of $NH_4OH$, and it was sonicated for 5 mins III. After sample redispersed in 10 ml of 4.2% (v/v) ethanol solution of $NH_4OH$, 43.5 μl of 10% (v/v) ethanol solution of TEOS was added to the previous solution containing the PS decorated with gold seeds under stirring, and the solution was kept in incubation over night to ensure a homogeneous silica coating. After silica coating, the sample was washed by 3 centrifugation cycles with ethanol (3500 rpm, 10 min).

4—Scaffold Dissolution:

For core dissolution, it means, hollow capsuled formation, the sediment from the last previous step was redispersed in a mixture solution 45 ml (EtOH:Chloroform=1:3), stirred for 36 h, in order to dissolve the core.

To verify the hollow capsules formation, the suspension was characterized by TEM. If the core was not completely removed, the sample was allowed for incubation in a new chloroform/ethanol mixture for one extra day and washed again after one day to check the core removal.

5—Gold Seeds Grown. Gold Seeds are Located in the Inner Walls of the Hollow Cavity.

I. 1 ml from Hollow silica capsules ethanolic solution with a concentration of 3.7 mg polystyrene/ml was added to 10 ml of Au+1 solution, stirred for 5 min, and followed by the addition of 30 microliters of commercial formaldehyde solution. This solution was stirred for 45 min, and after washed using three centrifugation cycles (3500 rpm, 10 min). Last two washing cycles were carried out in ethanol, after the last centrifugation cycle the sample was redisperse in a final volume of 2 ml (EtOH).

II. $Gold^{+1}$ solution: 433.46 microliters of 0.1206M $HAuCl_4$ solution was added to 120 ml of aqueous solution containing 1.8M of $K_2CO_3$. This solution must to be incubated in darkness place along 1 h before to use. Colour changed from yellow to colorless, and it implied that the gold 3 was turned into gold 1.

6—Outer Silica Shell Bio-Functionalization with Anti-ZIP4 Antibodies Via EDC Chemistry.

I. Mix 500 μL capsule suspension (0.83 mg mL-1, in ethanol) with APS (~1 APS molecule nm-2), and stirring at 60-70° C. for 90 min (in water bath)

II. Hollow silica capsules were centrifuged at 2500 rpm for 15 min and washed with ethanol and PBS, respectively.

III. Pre-Preparation “solution A”: 3.5 mg of dodecanedioic acid were dissolved in 0.5 mL of ethanol with 50 μL of aqueous NaOH solution (concentration: $1*10^{-3}$ M, pH basic around 8)

IV. Pre-Prepare EDAC (1-ethyl-3-(3-dimethylaminopropyl)-carbo-diimide) conjugation buffer: 2% (w/v) EDAC, 3% (w/v) N-hydroxysuccinimide in PBS, pH 8.0

V. Dodecanedioic acid buffer (3.5 mg) was mixed with 50 μL of EDAC conjugation buffer in an orbital shaker for 15 min at room temperature.

VI. hollow capsules (with APS) from the last step were incubated in “solution A” in an orbital shaker or vertex at room temperature; after 2 h, the reaction was quenched with 10 μL of 1 M hydroxylamine (NHS) (react for 5-10 min). (to regenerate the original, non-reacted carboxylic groups);

VII. Carboxylic acid-conjugated capsules were centrifuged at 5000 rpm for 15 min and washed with PBS (3×0.5 mL). Redisperse the capsules with PBS (centrifuge 3 times)

VIII. Ab conjugation: mix the 50 μL EDAC conjugation buffer and capsule with —COOH groups on surface, stirring for 15 min at RT; add 10 μg Ab into the capsule's mixture, keep the reaction for 2h; quench the reaction with 10 μL of 1 M hydroxylamine (react for 5-10 min).

IX. Centrifuge the Ab-functionalized capsules at 8000 rpm for 5 min and washed with PBS (3× 0.5 mL), and keep at 4° C.

Example 1.2. Synthesis of Bovine Serum Albumin (BSA) Nanoparticles 10 mg/mL BSA solution was prepared. First, BSA was dissolved in Milli-Q water (pH was around 5.3), an aliquot was taken, and pH shifted to of 7.4. Separately, 6 mL of absolute ethanol was added dropwise to 3 mL of the BSA solution previously prepared under vigorous stirring at room temperature. The solution turned turbid due to the formation of nanoparticles and 30 μL of glutaraldehyde 8% were quickly added. The resulting colloids were left stirring for 2 hours.

Example 1.3. Synthesis of Paclitaxel (PTX)-Loaded BSA Nanoparticles 10 mg/mL of BSA were dissolved in phosphate buffer 2 mM at pH 7.4. 1 mL of 1 mg/mL of Paclitaxel dissolved in absolute ethanol was added dropwise to 3 mL of BSA solution followed by another 5 mL of absolute ethanol under vigorous stirring at room temperature. Immediately afterwards, 10 μL of glutaraldehyde 8% was added per each mL of BSA solution. The final solution was left stirring for 2 hours.

Example 1.4. Characterisation of Nanoparticles

A Zetasizer nano series from Malvern was used to determine the hydrodynamic diameter and the zeta potential of nanoparticles. For the Dynamic Light Scattering (DLS) measurements, as synthesized NPs were diluted 10 times in Millli-Q water and samples were measured at 25° C. Similarly, nanoparticles were diluted 10 times in a 20 μM NaCl solution and Zeta potential measurements were conducted at 25° C.

Example 1.5. Cells

HEK293 and RWP1 cells were used to generate control cells and constitutively expressing Zip4 by transient transfecting pMSCV-IRES-Puro and pMSCV-Zip4-IRES-Puro plasmids respectively. Transfected cells were selected with 2 μg/ml puromycin and maintained with 0.25 μg/ml puromycin in DMEM containing 10% fetal bovine serum (FBS).

Example 1.6. Xenograft Experiment $7.5\times10^5$ cells were injected on one flank of BALB/c nude animals using 1:1 proportion DMEM: Matrigel. Tumors grew until reaching and average of 100 $mm^3$ (between 6-8 weeks). Then, 100 μl with 0.6 μg/μl red fluorescent nanoparticles were injected intravenously. 24 h later animals were sacrificed, and fluorescence was measured using an using Xenogen IVIS Spectrum equipment.

Example 1.7. Western Blot

Cells and tumors were homogenized in lysis buffer (50 mM Tris-HCl pH 7.4, 150 mM NaCl, 5 mM EDTA, 0.5% NP40, 1 mM DTT and EDTA-free protease inhibition cocktail, ROCHE 11873580001). Extracts were centrifuged at 14,000×g at 4° C. for 10 min to remove aggregates. Laemmli buffer was added and samples were boiled at 95° C. for 5 min and then loaded onto a 10% poly-acrylamide gel. After electrophoresis, proteins were transferred to nitro-cellulose membranes using the iBlot system (Invitrogen); membranes were then blocked with 5% BSA for 1 h at room temperature (RT). Primary Abs were diluted in blocking solution O/N at 4° C.: anti Zip4 (Proteintech), monoclonal antibodies anti Zip4, clones 33 and 62, and GAPDH (1:2000; Sigma-Aldrich). Anti-rabbit or anti-mouse HRP secondary Abs (1:2000; GE Healthcare) were used.

Example 1.8. Immunostaining

Paraffin sections (5 μm) were used for IHC analysis. Samples were boiled with 0.01 M citrate buffer (pH 6.0) at 120° C. for 10 min in a pressure cooker. Endogenous peroxidase activity was quenched with 3% H2O2, and samples were blocked in PBS with 1% BSA. Primary antibodies were added overnight at 4° C. As primary antibody rabbit α-anti Zip4 polyclonal antibody (Proteintech) was used. HRP-anti-rabbit-EnVision (DAKO, EnVision™+ System) was used as a secondary antibody.

Example 1.9. Surface Immunostaining

Cells were incubated with 50 μg/ml monoclonal antibodies in DMEM for 1 h at 37° C. After washing with PBS, cells were fixed in 4% PFA. The blocking was done incubating with 1% BSA and 2% FBS in PBS for 1 h RT. Incubation with secondary mouse Alexa 488 antibody (1:2000) was done in blocking solution for 1 h RT. Images were taken in a SP8 Leica confocal microscope.

Example 1.10. Sequencing of the Variable Region of the Antibodies

Sequencing of variable regions of 2 hybridoma cell line antibodies was carried out in the context of the present invention.

Total RNA was extracted from the hybridoma cells and cDNA was subsequently synthesized. Antibody variable genes were then amplified by isotype-specific PCR, subcloned into a standard cloning vector separately and sequenced.

The material used was:

Hybridoma cells.

TaKaRa MiniBEST Universal RNA Extraction Kit (Takara, Lot. No. 9767).

PrimeScript RT reagent Kit with gDNA Eraser (Takara, Lot. No. AK3920).

TA-cloning Kit (Takara, Lot. No. 6019).

PacBio RS II sequencer.

Total RNA was extracted separately from several batches of cultured hybridoma cells, cDNA was then synthetized by reverse transcription using oligo-dT primers and VH and VL were finally amplified by PCR. VH and VL fragments, respectively amplified by IgG degenerate primers and Kappa specific primers, were by gel electrophoresis, confirming that isotype is IgG Kappa. The PCR products were then sub-cloned into a standard vector, followed by bacteria transformation, then colony picking and validation by PCR and finally sequencing of 6-12 positive clones for each VH and VL.

Experiments were repeated twice, and identical results were obtained for all clones.

Thus, both hybridomas have been successfully sequenced. Results show that both antibodies have different VL but identical VH sequences. Two hypotheses could explain this finding:

1. Both clones originate from a unique one and only its VL has undergone further rearrangement and/or mutations.

2. Clones are different but have been selected for their identical VH.

The variable sequence of each antibody is shown below:

Antibody 1 (clone 33)

Heavy Chain Variable Region (VH)

DNA sequence (CDRs underlined: FR1-CDR1-FR2-CDR2-FR3-CDR3-FR4) (351 bp) (SEQ ID NO: 2):

GAGGTGAAGCTGCAGGAGTCAGGACCTAGCCTCGTGAAACCTTCTCAGT
CTCTGTCTCTCACCTGCTCTGTCACTGGCTACTCCATCACCAGTGCTTA
TTACTGGAACTGGATCCGGCAGTTTCCAGGAAACAAACTGGAATGGATG
GGCTACATAGCCTACGACGGTGGCAATAACTACAACCCATCTCTCAAAA
ATCGAATCTCCATCACTCGTGACACATCTAAGAACCAGTTTTTCCTGAA
GTTGAATTCTGTGACTACTGAGGACACAGCTACATATTACTGTGTAAGA
GATTGGTCACGGGCTATGGACTACTGGGGTCAAGGAACCTCAGTCACCG
TCTCCTCA

Amino acid sequence (CDRs underlined: FR1-CDR1-FR2-CDR2-FR3-CDR3-FR4) (117 amino acids) (SEQ ID NO:3):

EVKLQESGPSLVKPSQSLSLTCSVTGYSITSAYYWNWIRQFPGNKLEWM
GYIAYDGGNNYNPSLKNRISITRDTSKNQFFLKLNSVTTEDTATYYCVR
DWSRAMDYWGQGTSVTVSS

Light Chain Variable Region (VL)

DNA sequence (CDRs underlined: FR1-CDR1-FR2-CDR2-FR3-CDR3-FR4) (336 bp) (SEQ ID NO: 7):

GATATCATGCTGACCCAATCTCCACTCTCCCTGCCTGTCAGTCTTGGAG
ATCAAGCCTCCATCTCTTGCAGATCTAGTCAGAGCCTTGTGCACAGTAC
TGGAAACACCTATTTACATTGGTACCTGCAGAAGCCAGGCCAGTCTCCA
AAGCTCCTGATCTACAAAGTTTCCAGCCGATTTTCTGGGGTCCCAGACA
GATTCAGTGGCAGTGGATCAGGGACAGATTTCACACTCAGGATCAGTAG
AGTGGAGGCTGACGATCTGGGAGTTTATTTCTGTTCTCAAACCACACAT
GTTCCGCTCACGTTCGGTGCTGGGACCAAGCTGGAGCTGAAA

Amino acid sequence (CDRs underlined: FR1-CDR1-FR2-CDR2-FR3-CDR3-FR4) (112 amino acids) (SEQ ID NO:8):

DIMLTQSPLSLPVSLGDQASISCRSSQSLVHSTGNTYLHWYLQKPGQSP
KLLIYKVSSRFSGVPDRFSGSGSGTDFTLRISRVEADDLGVYFCSQTTH
VPLTFGAGTKLELK

Antibody 2 (clone 62):

Heavy Chain Variable Region (VH)

DNA sequence (CDRs underlined: FR1-CDR1-FR2-CDR2-FR3-CDR3-FR4) (351 bp) (SEQ ID NO: 11):

GAGGTGAAGCTGCAGGAGTCAGGACCTAGCCTCGTGAAACCTTCTCAGT
CTCTGTCTCTCACCTGCTCTGTCACTGGCTACTCCATCACCAGTGCTTA

-continued

TTACTGGAACTGGATCCGGCAGTTTCCAGGAAACAAACTGGAATGGATG
GGCTACATAGCCTACGACGGTGGCAATAACTACAACCCATCTCTCAAAA
ATCGAATCTCCATCACTCGTGACACATCTAAGAACCAGTTTTTCCTGAA
GTTGAATTCTGTGACTACTGAGGACACAGCTACATATTACTGTGTAAGA
GATTGGTCACGGGCTATGGACTACTGGGGTCAAGGAACCTCAGTCACCG
TCTCCTCA

Amino acid sequence (CDRs underlined: FR1-CDR1-FR2-CDR2-FR3-CDR3-FR4) (117 amino acids) (SEQ ID NO: 12):

EVKLQESGPSLVKPSQSLSLTCSVTGYSITSAYYWNWIRQFPGNKLEWM
GYIAYDGGNNYNPSLKNRISITRDTSKNQFFLKLNSVTTEDTATYYCVR
DWSRAMDYWGQGTSVTVSS

Light Chain Variable Region (VL)

DNA sequence (CDRs underlined: FR1-CDR1-FR2-CDR2-FR3-CDR3-FR4) (318 bp) (SEQ ID NO: 16):

GATATCGTTCTCACTCAATCTCCAGCAATCATGTCTGCATCTCCAGGGG
AGAAGGTCACCATAACCTGCAGTGCCAGCTCAAGTGTAAGTTACTTGCA
CTGGTTCCAGCAGAAGCCAGGCACTTCTCCCAAACTCTGGATTTATAGC
ACATCCAACCTGGCTTCTGGAGTCCCTGCTCGCTTCAGTGCCAGTGGAT
CTGGGACCTCTTACTCTCTCACAATCAGCCGAATGGAGGCTGAAGATGC
TGCCACTTATTACTGCCAACAAAGGAGTACTTATCCGCTCACGTTCGGT
GGTGGGACCAAGCTGGAGCTGAAA

Amino acid sequence (CDRs underlined: FR1-CDR1-FR2-CDR2-FR3-CDR3-FR4) (106 amino acids) (SEQ ID NO: 17):

DIVLTQSPAIMSASPGEKVTITCSASSSVSYLHWFQQKPGTSPKLWIYS
TSNLASGVPARFSASGSGTSYSLTISRMEAEDAATYYCQQRSTYPLTFG
GGTKLELK

The sequence listing is herewith included:

Antibody 1 (Clone 33)

- VH DNA sequence SEQ ID NO: 2
- VH amino acid sequence SEQ ID NO: 3
  - HCDR1 SEQ ID NO: 4
  - HCDR2 SEQ ID NO: 5
  - HCDR3 SEQ ID NO: 6
- VL DNA sequence SEQ ID NO: 7
- VL amino acid sequence SEQ ID NO: 8
  - LCDR1 SEQ ID NO: 9
  - LCDR2 consisting of KVS (Lys Val Ser)
  - LCDR3 SEQ ID NO: 10

Antibody 2 (Clone 62)

- VH DNA sequence SEQ ID NO: 11
- VH amino acid sequence SEQ ID NO: 12
  - HCDR1 SEQ ID NO: 13
  - HCDR2 SEQ ID NO: 14
  - HCDR3 SEQ ID NO: 15

VL DNA sequence SEQ ID NO: 16
VL amino acid sequence SEQ ID NO: 17
LCDR1 SEQ ID NO: 18
LCDR2 consisting of STS (Ser Thr Ser)
LCDR3 SEQ ID NO: 19

Example 2. Results

Example 2.1. Silica Hollow Nanocapsules with Crosslinked antiZip4 Antibody

We have synthetized biocompatible silica hollow nanocapsules to target Zip4 expressing tumoral cells using a layer by layer approach. By transmission electron microscopy we observed that the size of our nanocarriers was lower than 500 nm and do not aggregate (FIG. 1A). We have validated the presence of antiZip4 antibody crosslinked to the outer layer by incubating the nanocapsules loaded with rhodamine with an Alexa 488 antirabbit antibody in confocal imaging (FIG. 1B). Both signals, the nanocapsule in red and the secondary in green, colocalize. We have further confirmed the presence of the antiZip4 antibody in the nanocapsules using similar approach but measuring emission in with a spectrophotometer (FIG. 1C).

The silica shell not only act as a platform for covalently antibodies attachment, silica shell also provides rigidity to the structure avoiding the collapsed of the structure after scaffold dissolution and protecting encapsulated molecules and drugs inside the cavity. In order to treat pancreatic cancer, we have created paclitaxel nanoparticles conjugated to BSA (FIG. 1D-E). BSA nanoparticles and paclitaxel-loaded BSA nanoparticles were synthesized following a desolvation-coacervation method at pH conditions of 7.4. DLS measurements showed a shift in the size of the hydrodynamic diameter of PTX-BSA NPs when compared with the BSA NPs synthesized under the same conditions (FIG. 1D). However, there was no observable change in the surface net charge (FIG. 1E). Nab-paclitaxel is the first line treatment for fit patients. Drug encapsulation and targeting will minimize the undesired drug toxic effect.

Example 2.2. In Vivo Targeting Ability

Figure 2:
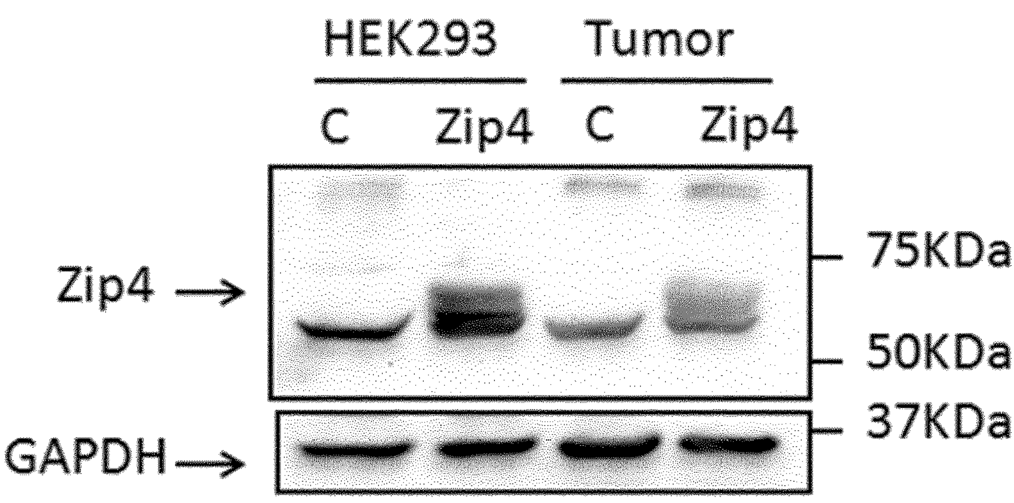
FIG. 2. In vivo targeting to Zip4 expressing tumor. A) Western blot against Zip4 and GAPDH of 100 μg of total lysate from HEK293 control cells and Zip4 expressing cells before injection (left) and after the tumor was grown (right). B) Immunohistochemistry against Zip4 of control HEK293 tumor and Zip4 HEK293 tumor from xenograft experiment. C) Representative IVIS image of ex vivo control HEK293 tumor and Zip4 HEK293 tumor after 24 h nanoparticle injection. D) Graph bar representing IVIS Fluorescence detection after 24 h injection in tumor xenografts of HEK293 control and Zip4 expressing HEK293 cells (SEM n=4 animals per condition; t-test; $*p<0.05$).
Figure 2:
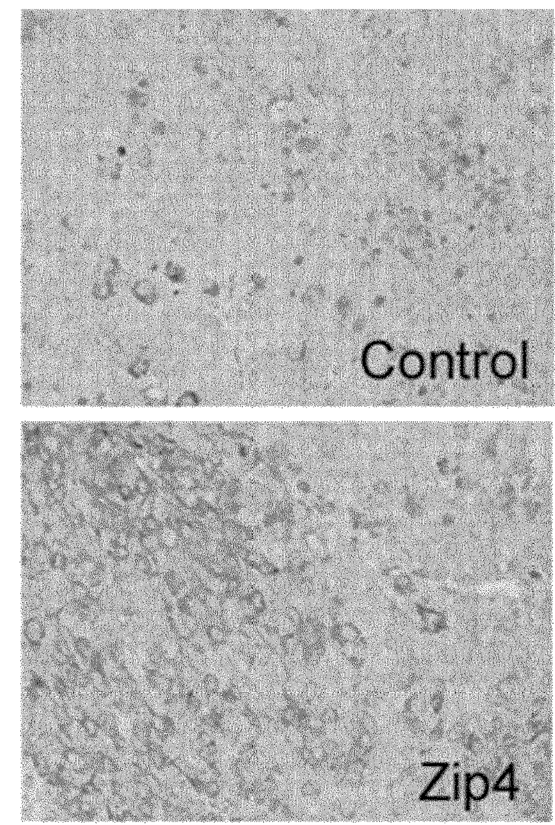
Figure 2:
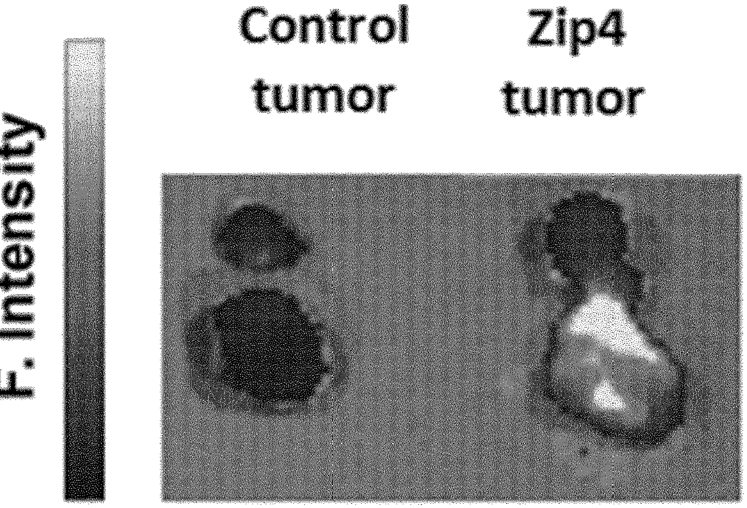
Figure 2:
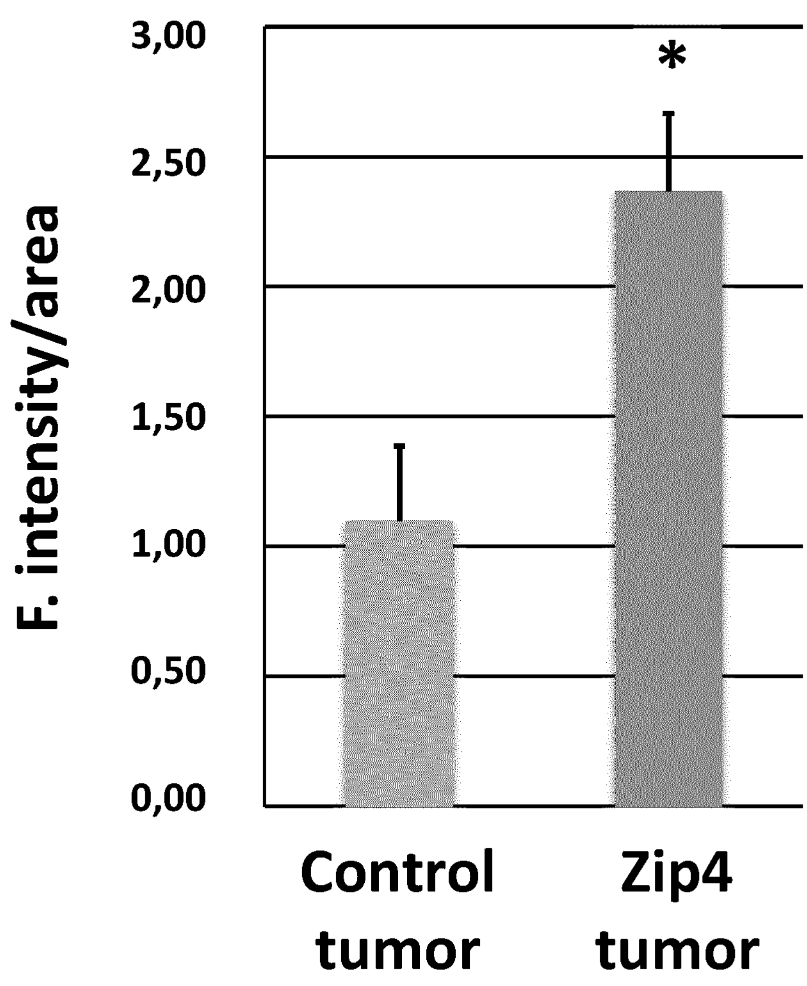

Once we generated the antiZIP4 nanocapsules we wanted to demonstrate the targeting ability of our nanoformulations in vivo. In order to do that, we have carried out a xenograft experiment using the HEK293 cell line expressing constitutively Zip4 transporter (FIG. 2). The expression of Zip4 in the tumors grown in the animals was validated by western blot (FIG. 2A) and immunohistochemistry (FIG. 2B). Once the tumors reached the 100 $mm^3$, we injected intravenously fluorescence antiZip4 nanocapsules. 24 h later, we measured nanoparticle accumulation in tumors detecting the fluorescence in an IVIS equipment. Our nanoparticles showed a higher accumulation in tumors expressing Zip4 than in control tumors (FIG. 2C-D). This result confirmed the ability of our nanoformulation to bind and accumulate in Zip4 expressing cells in vivo allowing drug delivery.

Example 2.3. Photothermal Activity

Figure 3:
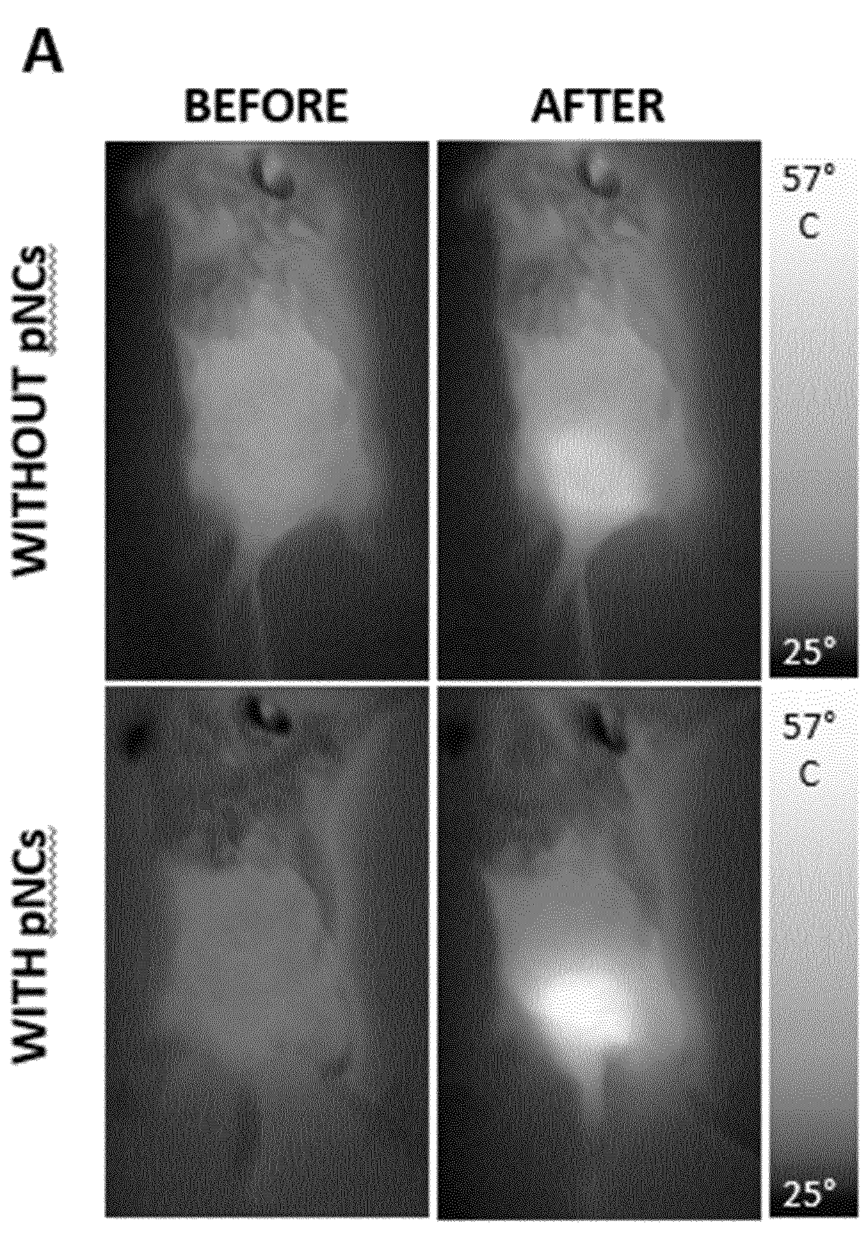
FIG. 3. Photothermal activity. A) and B) show the temperature increase after intratumoral administration of the nanocapsules and laser excitation (1.5 $W/cm^2$) measured with a photothermal camera. A) shows the heat distribution within the animal, B) shows the temperature increase over time and C) shows the effect of the nanoparticle-assisted increase in temperature on the reduction of tumor volume with no influence on weight. Abbreviations: pNCs: plasmonic nanocapsules (nanocapsules containing discrete gold nanoislands); min, minutes; PTT, photothermal; NCs and NCs+PTT indicates mice treated with the nanocapsules and no light irradiation and mice treated with nanocapsules and light irradiation to activate the photothermal effect, respectively.
Figure 3:
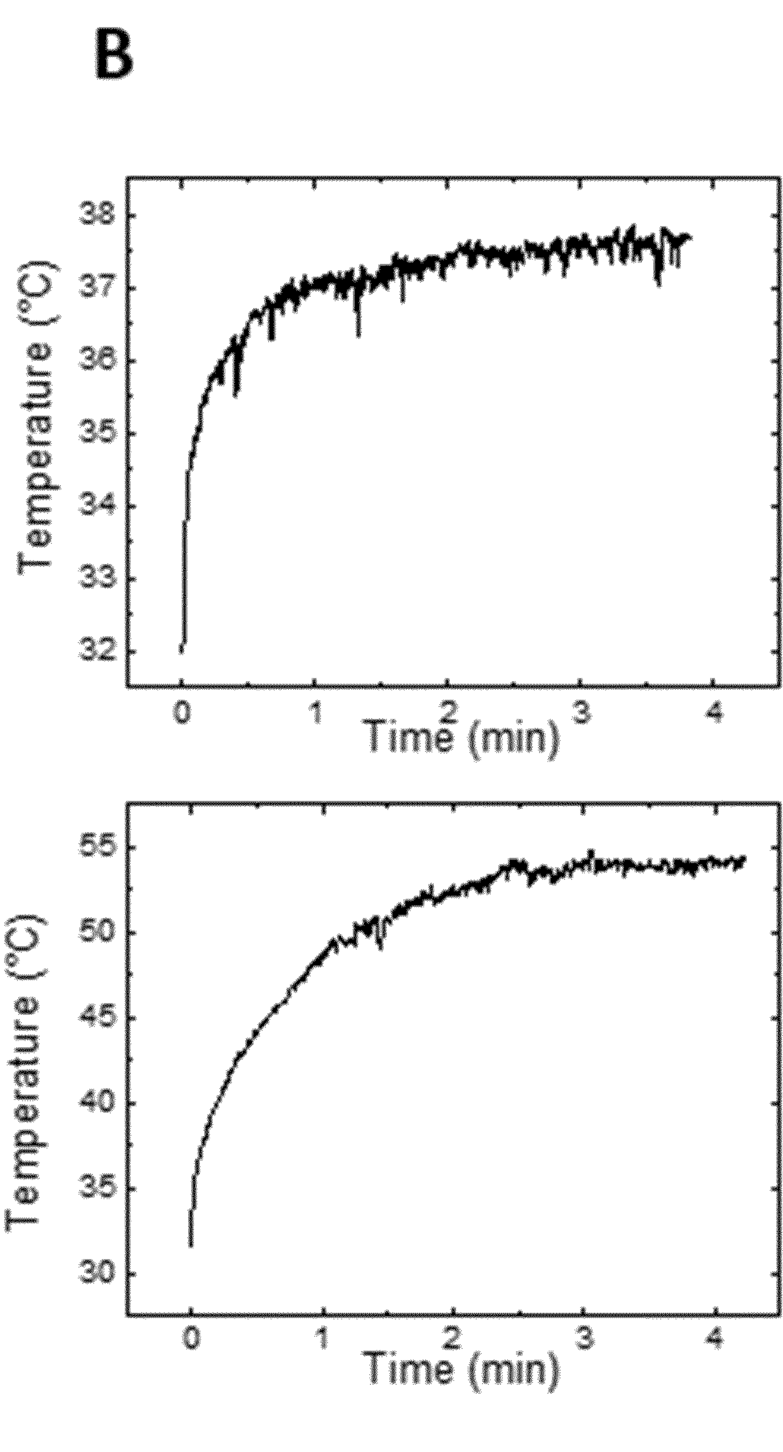
Figure 3:
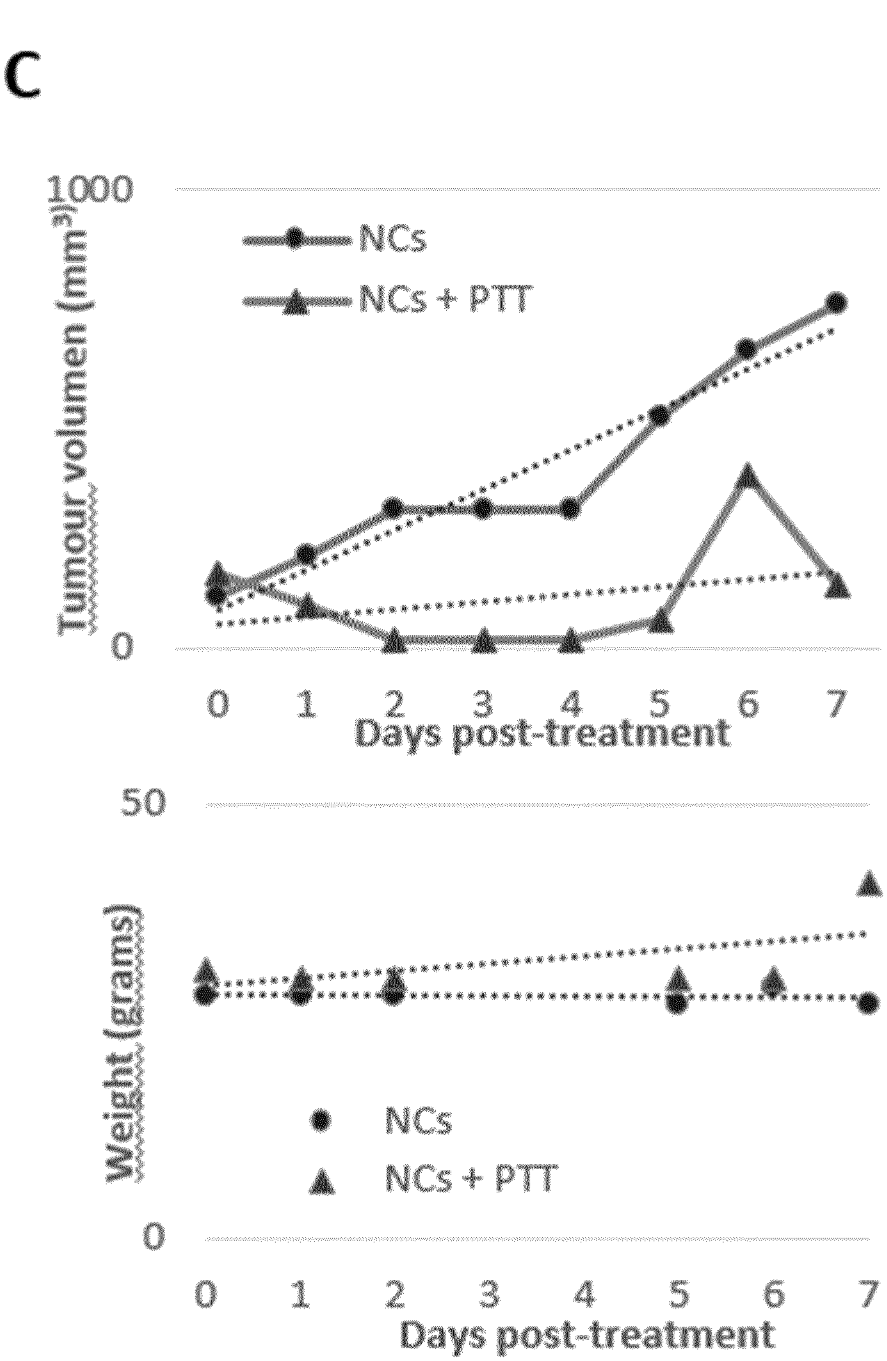

The nanocapsules are functionalized with discrete gold nanoislands to carry out photothermal therapy. FIG. 3A shows the increase of temperature in the tumor of an animal administered with gold nanocapsules upon laser irradiation compared with animals without nanocapsules. The superficial temperature rose locally and temporally until 55° C. (FIG. 3B). The nanocapsule-assisted thermal effect produced a reduction in the tumor growth without affecting the animal weight (FIG. 3C). The photothermal properties of these nanocapsules open a wide range of therapeutic approaches.

Example 2.4. Monoclonal antiZip4 Antibodies

Figure 4:
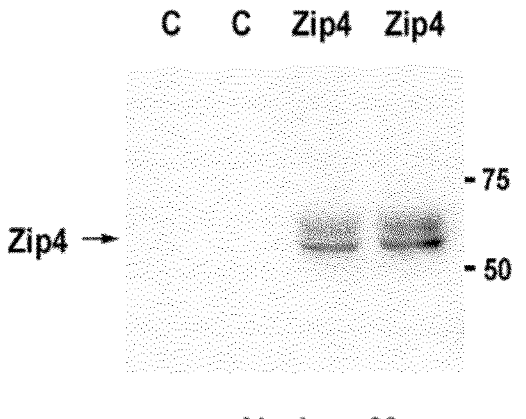
FIG. 4. Zip4 monoclonal antibodies specifically biding SEQ ID NO: 1. A) and B) show western blots against Zip4 of 100 μg of total lysate from RWP1 control cells (C) and Zip4 expressing RWP1 cells (Zip4). A) Representative western blot using monoclonal antibody clone 33. A) Representative western blot using monoclonal antibody clone 62. C) and D) show surface immunostaining against Zip4 in Zip4 expressing RWP1 cells incubated with clone 33 and clone 62 respectively.
Figure 4:
Figure 4:
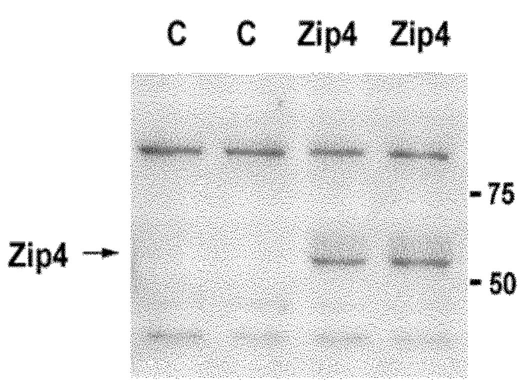
Figure 4:
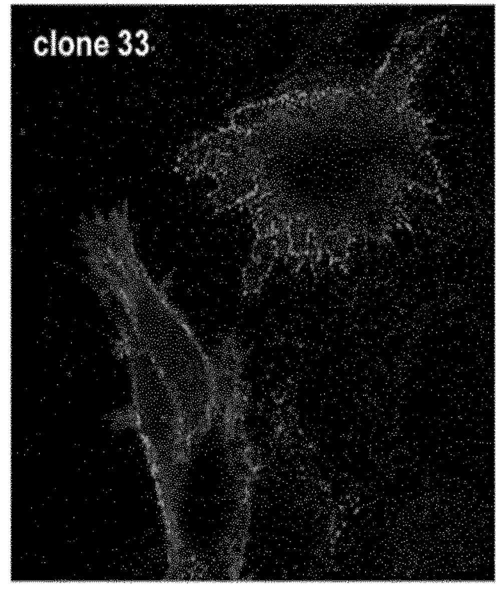
Figure 4:
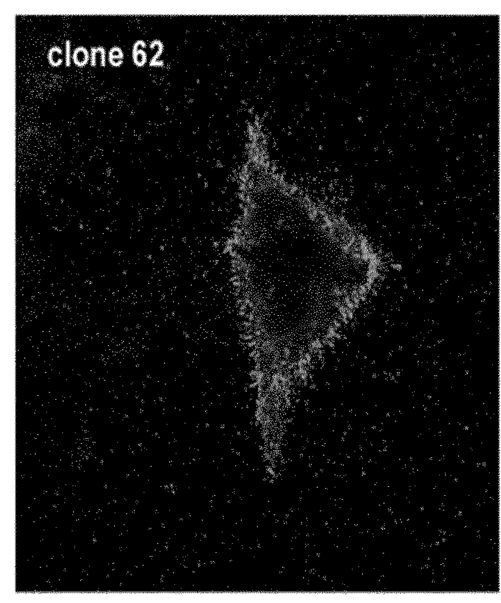

We studied the specificity of two novel monoclonal antibodies generated in our laboratory against human Zip4 extracellular domain (SEQ ID NO: 1). Two different antibodies, antibody 1 (clone 33) and antibody 2 (clone 62), from mouse hybridoma were characterized. We confirmed specificity by western blot using lysates from RWP1 cells constitutively expressing Zip4 (Zip4-RWP1 cells) and the control cell line (FIG. 4A-B). Both antibodies showed bands around 65 kDa that do not appear in control cells. Then, we characterized the binding properties in vivo of the antibody 1 and antibody 2 (clones 33 and 62, respectively) against Zip4 at the cell surface. We incubated for 1 h at 37° C. the antibodies with Zip4-RWP1 cells before washing and fixing. We obtained a plasma membrane staining with both antibodies (FIG. 4C-D).

The invention claimed is:

1. A method of using a nanocarrier in the treatment and/or diagnosis of a cancer, the method comprising:

functionalizing the nanocarrier with an affinity reagent, wherein the affinity reagent comprises a monoclonal antibody comprising:

a light chain variable region (VL) comprising LCDR1, LCDR2, and LCDR3 polypeptides; and a heavy chain variable region (VH) comprising HCDR1, HCDR2, and HCDR3 polypeptides, wherein the HCDR1 comprises the sequence of SEQ ID NO: 4, wherein the HCDR2 comprises the sequence of SEQ ID NO: 5, wherein the HCDR3 comprises the sequence of SEQ ID NO: 6, wherein the LCDR1 comprises the sequence of SEQ ID NO: 9, wherein the LCDR2 comprises KVS, wherein the LCDR3 comprises the sequence of SEQ ID NO: 10;

wherein the affinity reagent binds to an extracellular domain of Zinc transporter ZIP4, wherein the extracellular domain of ZIP4 comprises the sequence of SEQ ID NO: 1, and wherein the cancer expresses ZIP4, and administering the functionalized nanocarrier to a subject.

2. The method of claim 1, wherein the affinity reagent comprises an antibody obtained by an in vitro method, the in vitro method comprising:

a) administering an immunogen of SEQ ID NO: 1 to an animal model to induce generation of antibodies, wherein SEQ ID NO: 1 includes the extracellular domain of Zinc transporter ZIP4; and b) obtaining the antibodies generated in step a).

3. The method of claim 1, wherein the affinity reagent comprises a monoclonal antibody comprising:

a light chain variable region (VL) comprising LCDR1, LCDR2, and LCDR3 polypeptides; and a heavy chain variable region (VH) comprising HCDR1, HCDR2, and HCDR3 polypeptides, wherein the HCDR1 comprises the sequence of SEQ ID NO: 13, wherein the HCDR2 comprises the sequence of SEQ ID NO: 14, wherein the HCDR3 comprises the sequence of SEQ ID NO: 15, wherein the LCDR1 comprises the sequence of SEQ ID NO: 18, wherein the LCDR2 comprises STS, and wherein the LCDR3 comprises the sequence of SEQ ID NO: 19.

4. The method of claim 1, wherein the affinity reagent comprises a monoclonal antibody, or fragment thereof.

5. The method of claim 1, wherein the cancer comprises a ZIP-related tumor.

6. The method of claim 5, wherein the cancer is pancreatic cancer.

7. The method of claim 5, wherein the nanocarrier transports and delivers an active ingredient to the ZIP-related tumor.

8. The method of claim 6, wherein the nanocarrier transports and delivers an active ingredient to the ZIP-related tumor.

9. The method of claim 1, wherein the nanocarrier comprises hollow nanocapsules, the nanocapsules comprising a biodegradable material on a layer basis around a sacrificial template with a size lower than 500 nm.

10. The method of claim 1, wherein the nanocarrier comprises an anti-cancer drug.

11. The method of claim 1, wherein the nanocarrier comprises an X-ray contrast agent.

12. The method of claim 1, wherein the nanocarrier transports and delivers an active ingredient to the cancer expressing the ZIP4.

* * * * *

SEQUENCE LISTING

```
<160> NUMBER OF SEQ ID NOS: 19

<210> SEQ ID NO 1
<211> LENGTH: 305
<212> TYPE: PRT
<213> ORGANISM: Artificial sequence
<220> FEATURE:
<223> OTHER INFORMATION: ZIP4 extracellular domain

<400> SEQUENCE: 1

Ser Pro Pro Ala Gly Leu Leu Ser Leu Leu Thr Ser Gly Gln Gly Ala
1               5                   10                  15

Leu Asp Gln Glu Ala Leu Gly Gly Leu Leu Asn Thr Leu Ala Asp Arg
            20                  25                  30

Val His Cys Ala Asn Gly Pro Cys Gly Lys Cys Leu Ser Val Glu Asp
        35                  40                  45

Ala Leu Gly Leu Gly Glu Pro Glu Gly Ser Gly Leu Pro Pro Gly Pro
```

```
    50                  55                  60

Val Leu Glu Ala Arg Tyr Val Ala Arg Leu Ser Ala Ala Ala Val Leu
65                  70                  75                  80

Tyr Leu Ser Asn Pro Glu Gly Thr Cys Glu Asp Ala Arg Ala Gly Leu
                85                  90                  95

Trp Ala Ser His Ala Asp His Leu Leu Ala Leu Leu Glu Ser Pro Lys
            100                 105                 110

Ala Leu Thr Pro Gly Leu Ser Trp Leu Leu Gln Arg Met Gln Ala Arg
        115                 120                 125

Ala Ala Gly Gln Thr Pro Lys Met Ala Cys Val Asp Ile Pro Gln Leu
    130                 135                 140

Leu Glu Glu Ala Val Gly Ala Gly Ala Pro Gly Ser Ala Gly Gly Val
145                 150                 155                 160

Leu Ala Ala Leu Leu Asp His Val Arg Ser Gly Ser Cys Phe His Ala
                165                 170                 175

Leu Pro Ser Pro Gln Tyr Phe Val Asp Phe Val Phe Gln Gln His Ser
            180                 185                 190

Ser Glu Val Pro Met Thr Leu Ala Glu Leu Ser Ala Leu Met Gln Arg
        195                 200                 205

Leu Gly Val Gly Arg Glu Ala His Ser Asp His Ser His Arg His Arg
    210                 215                 220

Gly Ala Ser Ser Arg Asp Pro Val Pro Leu Ile Ser Ser Ser Asn Ser
225                 230                 235                 240

Ser Ser Val Trp Asp Thr Val Cys Leu Ser Ala Arg Asp Val Met Ala
                245                 250                 255

Ala Tyr Gly Leu Ser Glu Gln Ala Gly Val Thr Pro Glu Ala Trp Ala
            260                 265                 270

Gln Leu Ser Pro Ala Leu Leu Gln Gln Gln Leu Ser Gly Ala Cys Thr
        275                 280                 285

Ser Gln Ser Arg Pro Pro Val Gln Asp Gln Leu Ser Gln Ser Glu Arg
    290                 295                 300

Tyr
305


<210> SEQ ID NO 2
<211> LENGTH: 351
<212> TYPE: DNA
<213> ORGANISM: Artificial sequence
<220> FEATURE:
<223> OTHER INFORMATION: VH sequence

<400> SEQUENCE: 2

gaggtgaagc tgcaggagtc aggacctagc ctcgtgaaac cttctcagtc tctgtctctc     60

acctgctctg tcactggcta ctccatcacc agtgcttatt actggaactg gatccggcag    120

tttccaggaa acaaactgga atggatgggc tacatagcct acgacggtgg caataactac    180

aacccatctc tcaaaaatcg aatctccatc actcgtgaca catctaagaa ccagtttttc    240

ctgaagttga attctgtgac tactgaggac acagctacat attactgtgt aagagattgg    300

tcacgggcta tggactactg gggtcaagga acctcagtca ccgtctcctc a             351


<210> SEQ ID NO 3
<211> LENGTH: 117
<212> TYPE: PRT
<213> ORGANISM: Artificial sequence
<220> FEATURE:
<223> OTHER INFORMATION: VH sequence
```

<400> SEQUENCE: 3

Glu Val Lys Leu Gln Glu Ser Gly Pro Ser Leu Val Lys Pro Ser Gln
1 5 10 15

Ser Leu Ser Leu Thr Cys Ser Val Thr Gly Tyr Ser Ile Thr Ser Ala
20 25 30

Tyr Tyr Trp Asn Trp Ile Arg Gln Phe Pro Gly Asn Lys Leu Glu Trp
35 40 45

Met Gly Tyr Ile Ala Tyr Asp Gly Gly Asn Asn Tyr Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys
85 90 95

Val Arg Asp Trp Ser Arg Ala Met Asp Tyr Trp Gly Gln Gly Thr Ser
100 105 110

Val Thr Val Ser Ser
115

<210> SEQ ID NO 4
<211> LENGTH: 9
<212> TYPE: PRT
<213> ORGANISM: Artificial sequence
<220> FEATURE:
<223> OTHER INFORMATION: HCDR1

<400> SEQUENCE: 4

Gly Tyr Ser Ile Thr Ser Ala Tyr Tyr
1 5

<210> SEQ ID NO 5
<211> LENGTH: 7
<212> TYPE: PRT
<213> ORGANISM: Artificial sequence
<220> FEATURE:
<223> OTHER INFORMATION: HCDR2

<400> SEQUENCE: 5

Ile Ala Tyr Asp Gly Gly Asn
1 5

<210> SEQ ID NO 6
<211> LENGTH: 10
<212> TYPE: PRT
<213> ORGANISM: Artificial sequence
<220> FEATURE:
<223> OTHER INFORMATION: HCDR3

<400> SEQUENCE: 6

Val Arg Asp Trp Ser Arg Ala Met Asp Tyr
1 5 10

<210> SEQ ID NO 7
<211> LENGTH: 336
<212> TYPE: DNA
<213> ORGANISM: Artificial sequence
<220> FEATURE:
<223> OTHER INFORMATION: VL sequence

<400> SEQUENCE: 7
gatatcatgc tgacccaatc tccactctcc ctgcctgtca gtcttggaga tcaagcctcc 60
atctcttgca gatctagtca gagccttgtg cacagtactg gaaacaccta tttacattgg 120

```
tacctgcaga agccaggcca gtctccaaag ctcctgatct acaaagtttc cagccgattt    180

tctggggtcc cagacagatt cagtggcagt ggatcaggga cagatttcac actcaggatc    240

agtagagtgg aggctgacga tctgggagtt tatttctgtt ctcaaaccac acatgttccg    300

ctcacgttcg gtgctgggac caagctggag ctgaaa                              336


<210> SEQ ID NO 8
<211> LENGTH: 112
<212> TYPE: PRT
<213> ORGANISM: Artificial sequence
<220> FEATURE:
<223> OTHER INFORMATION: VL sequence

<400> SEQUENCE: 8

Asp Ile Met Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Leu Gly Val Tyr Phe Cys Ser Gln Thr
                85                  90                  95

Thr His Val Pro Leu Thr Phe Gly Ala Gly Thr Lys Leu Glu Leu Lys
            100                 105                 110


<210> SEQ ID NO 9
<211> LENGTH: 11
<212> TYPE: PRT
<213> ORGANISM: Artificial sequence
<220> FEATURE:
<223> OTHER INFORMATION: LCDR1

<400> SEQUENCE: 9

Gln Ser Leu Val His Ser Thr Gly Asn Thr Tyr
1               5                   10


<210> SEQ ID NO 10
<211> LENGTH: 9
<212> TYPE: PRT
<213> ORGANISM: Artificial sequence
<220> FEATURE:
<223> OTHER INFORMATION: LCDR3

<400> SEQUENCE: 10

Ser Gln Thr Thr His Val Pro Leu Thr
1               5


<210> SEQ ID NO 11
<211> LENGTH: 351
<212> TYPE: DNA
<213> ORGANISM: Artificial sequence
<220> FEATURE:
<223> OTHER INFORMATION: VH sequence

<400> SEQUENCE: 11

gaggtgaagc tgcaggagtc aggacctagc ctcgtgaaac cttctcagtc tctgtctctc     60

acctgctctg tcactggcta ctccatcacc agtgcttatt actggaactg gatccggcag    120
```

```
tttccaggaa acaaactgga atggatgggc tacatagcct acgacggtgg caataactac    180

aacccatctc tcaaaaatcg aatctccatc actcgtgaca catctaagaa ccagtttttc    240

ctgaagttga attctgtgac tactgaggac acagctacat attactgtgt aagagattgg    300

tcacgggcta tggactactg gggtcaagga acctcagtca ccgtctcctc a             351
```

```
<210> SEQ ID NO 12
<211> LENGTH: 117
<212> TYPE: PRT
<213> ORGANISM: Artificial sequence
<220> FEATURE:
<223> OTHER INFORMATION: VH sequence

<400> SEQUENCE: 12

Glu Val Lys Leu Gln Glu Ser Gly Pro Ser Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ala Tyr Asp Gly Gly Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Val Arg Asp Trp Ser Arg Ala Met Asp Tyr Trp Gly Gln Gly Thr Ser
            100                 105                 110

Val Thr Val Ser Ser
        115


<210> SEQ ID NO 13
<211> LENGTH: 9
<212> TYPE: PRT
<213> ORGANISM: Artificial sequence
<220> FEATURE:
<223> OTHER INFORMATION: HCDR1

<400> SEQUENCE: 13

Gly Tyr Ser Ile Thr Ser Ala Tyr Tyr
1               5


<210> SEQ ID NO 14
<211> LENGTH: 7
<212> TYPE: PRT
<213> ORGANISM: Artificial sequence
<220> FEATURE:
<223> OTHER INFORMATION: HCDR2

<400> SEQUENCE: 14

Ile Ala Tyr Asp Gly Gly Asn
1               5


<210> SEQ ID NO 15
<211> LENGTH: 10
<212> TYPE: PRT
<213> ORGANISM: Artificial sequence
<220> FEATURE:
<223> OTHER INFORMATION: HCDR3

<400> SEQUENCE: 15
```

```
Val Arg Asp Trp Ser Arg Ala Met Asp Tyr
1               5                   10


<210> SEQ ID NO 16
<211> LENGTH: 318
<212> TYPE: DNA
<213> ORGANISM: Artificial sequence
<220> FEATURE:
<223> OTHER INFORMATION: VL sequence

<400> SEQUENCE: 16

gatatcgttc tcactcaatc tccagcaatc atgtctgcat ctccagggga gaaggtcacc     60

ataacctgca gtgccagctc aagtgtaagt tacttgcact ggttccagca gaagccaggc    120

acttctccca aactctggat ttatagcaca tccaacctgg cttctggagt ccctgctcgc    180

ttcagtgcca gtggatctgg gacctcttac tctctcacaa tcagccgaat ggaggctgaa    240

gatgctgcca cttattactg ccaacaaagg agtacttatc cgctcacgtt cggtggtggg    300

accaagctgg agctgaaa                                                  318


<210> SEQ ID NO 17
<211> LENGTH: 106
<212> TYPE: PRT
<213> ORGANISM: Artificial sequence
<220> FEATURE:
<223> OTHER INFORMATION: VL sequence

<400> SEQUENCE: 17

Asp Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Leu
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Ala Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Thr Tyr Pro Leu Thr
                85                  90                  95

Phe Gly Gly Gly Thr Lys Leu Glu Leu Lys
            100                 105


<210> SEQ ID NO 18
<211> LENGTH: 5
<212> TYPE: PRT
<213> ORGANISM: Artificial sequence
<220> FEATURE:
<223> OTHER INFORMATION: LCDR1

<400> SEQUENCE: 18

Ser Ser Val Ser Tyr
1               5


<210> SEQ ID NO 19
<211> LENGTH: 9
<212> TYPE: PRT
<213> ORGANISM: Artificial sequence
```

-continued

```
<220> FEATURE:
<223> OTHER INFORMATION: LCDR3

<400> SEQUENCE: 19

Gln Gln Arg Ser Thr Tyr Pro Leu Thr
1               5
```